(12) United States Patent
Nino et al.

(10) Patent No.: US 9,603,673 B2
(45) Date of Patent: Mar. 28, 2017

(54) ULTRA HIGH TORQUE DEVICE

(71) Applicant: ECA Medical Instruments, Newbury Park, CA (US)

(72) Inventors: John Nino, Simi Valley, CA (US); David Ivinson, Camarillo, CA (US)

(73) Assignee: ECA Medical Instruments, Newbury Park, CA (US)

( * ) Notice: Subject to any disclaimer, the term of this patent is extended or adjusted under 35 U.S.C. 154(b) by 0 days.

(21) Appl. No.: 15/298,812

(22) Filed: Oct. 20, 2016

(65) Prior Publication Data

US 2017/0049526 A1    Feb. 23, 2017

Related U.S. Application Data

(63) Continuation of application No. 14/202,855, filed on Mar. 10, 2014, now Pat. No. 9,504,479.

(60) Provisional application No. 61/776,337, filed on Mar. 11, 2013.

(51) Int. Cl.
| | |
|---|---|
| *A61B 17/00* | (2006.01) |
| *A61B 90/00* | (2016.01) |
| *A61B 17/16* | (2006.01) |
| *A61B 17/32* | (2006.01) |

(52) U.S. Cl.
CPC ........ *A61B 90/03* (2016.02); *A61B 17/00234* (2013.01); *A61B 17/1671* (2013.01); *A61B 17/320016* (2013.01); *A61B 2090/031* (2016.02)

(58) Field of Classification Search
None
See application file for complete search history.

(56) References Cited

U.S. PATENT DOCUMENTS

| | | | |
|---|---|---|---|
| 7,938,046 B2 | 5/2011 | Nino et al. | |
| 8,690,884 B2 * | 4/2014 | Linderman | ........ A61B 17/8811 606/94 |

* cited by examiner

*Primary Examiner* — Sameh Boles
(74) *Attorney, Agent, or Firm* — Baker & Hostetler LLP (57) ABSTRACT

A device and method of delivering a medical tool which may be a resector, cutter, probe, or the like, including a memory arm compacted in a small diameter state which expands in a relaxed memory state, is disclosed. Said delivery may include using a hollow sheath to pre-compact or preload a memory blade into a compact position, transferring said compacted memory blade into a cannula, and deploying said memory blade from the distal end of said cannula whereby the memory blade returns to its normal expanded memory state and a deployment nut can be used to control the extension or the withdrawal of the memory arm and blade.

4 Claims, 8 Drawing Sheets

FIG. 12

ULTRA HIGH TORQUE DEVICE

CROSS REFERENCE TO RELATED APPLICATION

This patent application is a Continuation of U.S. Utility patent application Ser. No. 14/202,855 filed Mar. 10, 2014, which claims benefit to U.S. Provisional Application No. 61/776,337 filed Mar. 11, 2013, the content of which are incorporated by this reference as if fully set forth herein their entirety.

BACKGROUND

1. Field

This disclosure relates to a resector for minimally invasive spinal.

2. General Background

Within a vertebra is cancelleous bone "A," see FIGS. 1A, 1B and 2A and 2B. Surrounding the cancellous bone is a Cortical rim "B," which is compared to compact bone. Compared to compact bone, cancellous has a higher surface area but is less dense, softer, weaker, and less stiff. It typically occurs at the ends of long bones, proximal to joints and within the interior of vertebrae. Cancellous bone is highly vascular and frequently contains red bone marrow where hematopoiesis, the production of blood cells, occurs. The primary anatomical and functional unit of cancellous bone is the trabecula. The vertebral body "C" includes both compact and cancellous bone.

One method to access the cancelleous bone of a vertebra is by way of a trocar "D." A trocar is a sharply pointed shaft, usually with a three-sided point. A trocar may be used within a cannula "E," a hollow tube, designed to be inserted into a vein, artery, bone marrow or body cavity. The word trocar is derived from the French "trois" (three)+"carre" (side).

Procedures used to address damage to vertebral bodies may include vertebroplasty and kyphoplasty, which are medical spinal procedures where bone cement is injected into a damaged or fractured vertebra with the goal of relieving the pain of osteoporotic compression fractures.

Vertebroplasty is typically performed by a spine surgeon or interventional radiologist. It is a minimally invasive procedure and patients usually go home on the same or next day as the procedure. Patients are given local anesthesia and light sedation for the procedure, though it can be performed using only local anesthetic for patients with medical problems who cannot tolerate sedatives well.

During a procedure, bone cement is injected with a biopsy needle into the collapsed or fractured vertebra. Access to the cancellous bone is via a needle through a resected hole. The bone cement dries and may form a support structure within the vertebra that provides stabilization and strength.

Cervical vertebra pose additional challenges as they are smaller scale than thoracic and lumbar vertebra. For minimally invasive, in particular in the cervical region access cannula may be as small as 11 gauge o.d.

DISCLOSURE

Disclosed herein are aspects of exemplary implementations of systems, devices and methods to perform minimally invasive surgery. Also, disclosed are systems methods and devices and aspects thereof to control the deployment of a memory arm with resector during such surgery. Also, disclosed are systems methods and devices and aspects thereof to move a compressed memory arm and resector blade (in a generally linear form factor) into a lumen for use in surgery.

Disclosed herein are aspects of exemplary implementations of systems, devices and methods to perform minimally invasive surgery on a vertebral body using a cannula including a handle with a shaft less than the internal diameter (i.d.) of a cannula having a memory arm with a blade attached thereto; the memory arm compactable to a substantially co-axial position within a cannula; a hollow sheath with a forward tip having an i.d. substantially the same as the diameter of the cannula; the memory arm compacted into said hollow sheath; the cannula having a distal and a proximal end; the cannula having an interior diameter substantially the same as the i.d. of said hollow sheath; and, whereby aligning the tip and the proximal end of the cannula provides a pathway for the compacted memory arm and blade to be passed in a compacted state from the hollow sheath into the cannula. In some instance the hollow cannula includes a mounting corresponding to the forward tip.

In some instances device includes a sheath sleeve with a forward end that fits over at least a portion of the hollow sheath; and, wherein the forward end of the sheath sleeve is threaded, and the handle facing side of the cannula mount has corresponding threads.

In some instances the sheath sleeve and hollow sheath are a unitary piece having the i.d. of the hollow sheath and the corresponding threading of the sheath sleeve. In some instances sleeve gripping elements extend radially around the sheath sleeve.

Disclosed herein are aspects of exemplary implementations of systems, devices and methods to perform minimally invasive surgery on a vertebral body using a cannula. The system includes a handle containing a rotatable torque limiting device; a shaft having an outer diameter (o.d.) of less than about 2.33 mm affixed at its proximal end to the torque limiting device; a memory arm formed as part of the shaft at the distal end of the shaft; a resector, tool or blade formed at the remote end of the arm; and, a hollow sheath with a forward tip having an i.d. of about 2.36 mm surrounding said memory arm and blade whereby said memory arm is compacted therein.

Disclosed herein are aspects of exemplary implementations of systems, devices and methods to perform minimally invasive surgery on a vertebral body using an 11 gauge cannula cannula having an i.d. substantially the same as the i.d. of a hollow sheath. The system includes a handle containing a rotatable torque limiting device; a shaft having an outer diameter (o.d.) of less than about 2.33 mm affixed at its proximal end to the torque limiting device; a memory arm formed as part of the shaft at the distal end of the shaft; a resector, tool or blade formed at the remote end of the arm; a hollow sheath with a forward tip having an i.d. of about 2.36 mm surrounding said memory arm and blade whereby said memory arm is compacted therein and, a temporary mount that connects the cannula with the forward tip aligning the sheath with the cannula wherein the blade and memory arm can be inserted into the cannula lumen while maintaining the memory arm's compacted state.

Disclosed herein are aspects of exemplary implementations of systems, devices and methods to perform minimally invasive surgery on a vertebral body having a resecting device with a handle having a neck; a shaft having a memory arm with a blade affixed at the distal end; the shaft affixed at its proximal end to said neck; a cannula with a body affixed at its proximal end; a lumen within said cannula having a larger i.d. than the o.d. of the shaft and compacted memory arm and blade; said memory arm and blade compacted within the lumen and slideable within the lumen whereby it may extend out of the cannula's distal end; an adjustable deployment nut movably mounted on the neck whereby it is movable co-axially on said neck; and, whereby the deployment nut engages the body and the movement of the deployment nut forward or back on the neck causes the memory arm and blade to slide in or out of the distal end of the cannula. In some instances the system of claim 9, wherein the neck and the deployment nut have corresponding threading. In some instances the resecting device also includes a hollow sheath, which holds the memory arm and blade in a compacted state allowing for passage to the lumen of the cannula maintaining the compacted state. In some instances that connection is via a body attached to the cannula's proximal end which mates with the hollow sheath.

Aspects of the system and method disclosed herein include deployment of a blade into a vertebral body via the controlled movement of a memory arm with a resector, tool or blade at its most distal end out of the distal end of a lumen wherein the position of a deployment nut along a threaded neck corresponds to such movement. One example is the movement of the deployment nut along the threaded neck from α and α' corresponds to extension of the memory arm form the lumen. In some instances one or more sensory positional reference marks are visible or available for tactile register on the neck. Tactile register refers to a bump, divot or other feature that can be felt.

DRAWINGS

The above-mentioned features of the present disclosure will become more apparent with reference to the following description taken in conjunction with the accompanying drawings wherein like reference numerals denote like elements and in which.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the figures are hereby incorporated by this reference as if fully set forth herein.

FURTHER DISCLOSURE

Figure 1A:
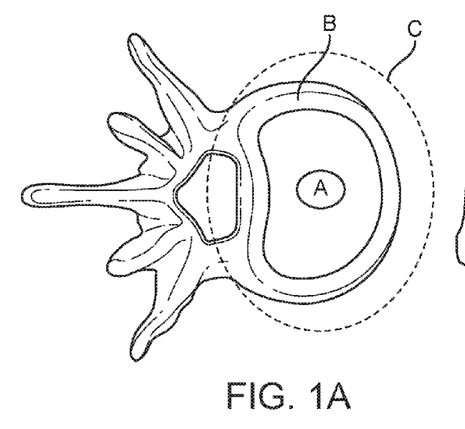
FIGS. 1A and 1B are top and side views of a vertebral body.
Figure 1B:
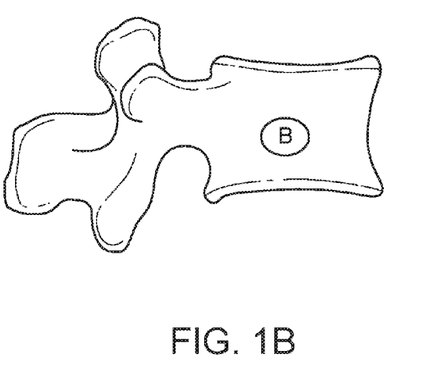
Figure 2A:
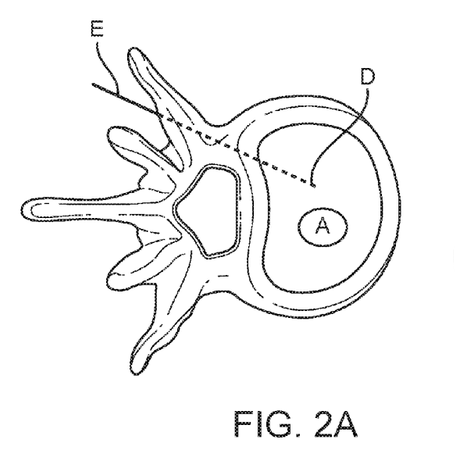
FIGS. 2A and 2B are top and side views of a trocar and/or cannula introduced through a vertebral body into cancelleous bone.
Figure 2B:
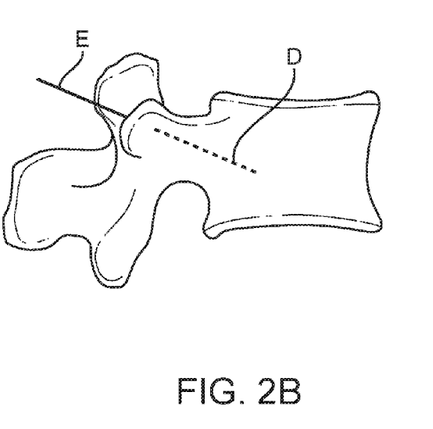
Figure 3:
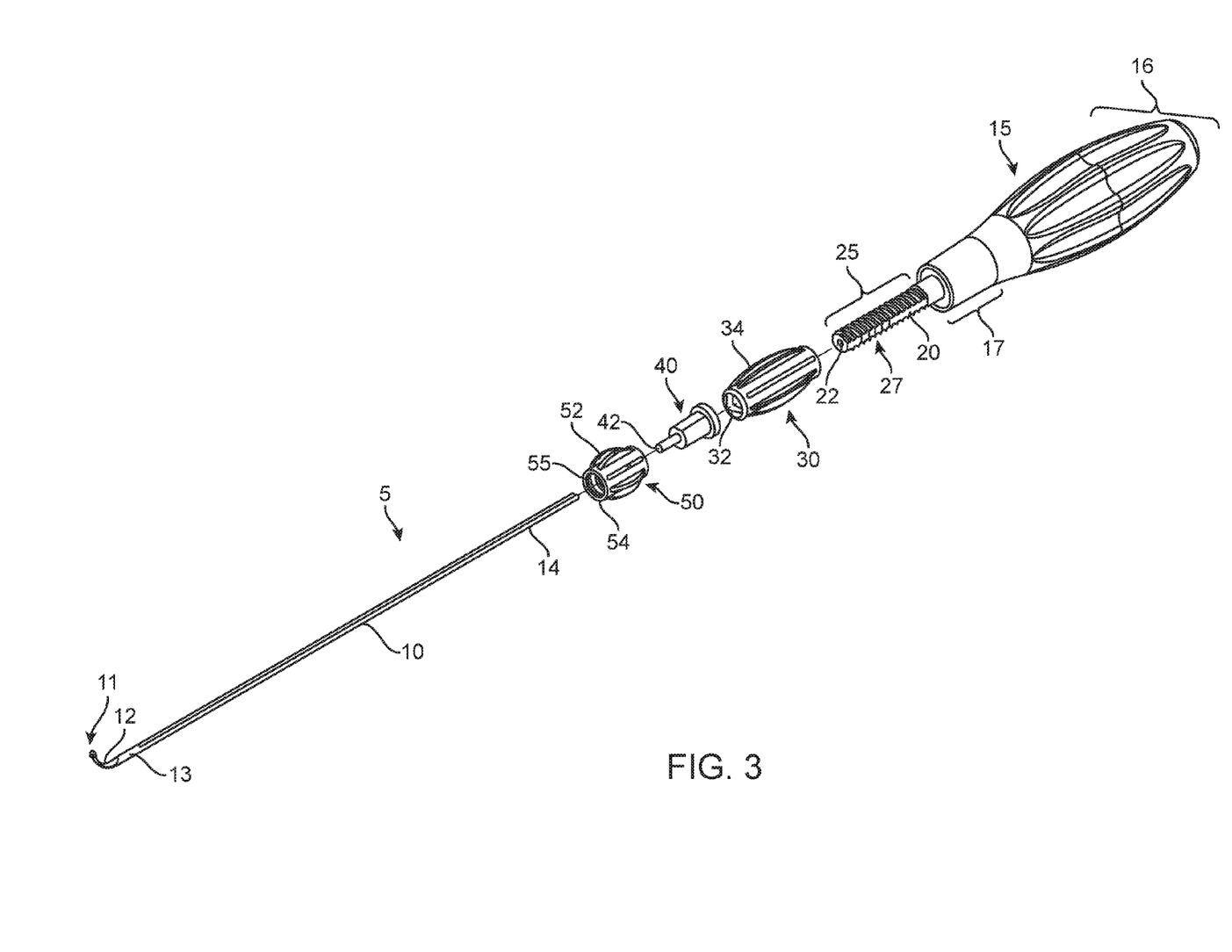
FIG. 3 shows an assembly view of a torque limiting device with extendable memory blade.
Figure 4:
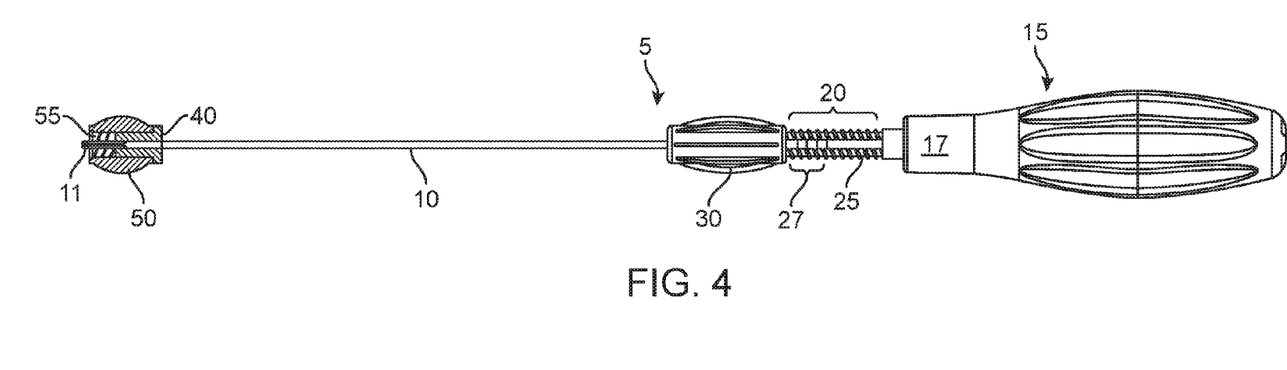
FIG. 4 shows a partial cutaway view of a torque limiting device with connector sheath extendable memory blade.
Figure 5:
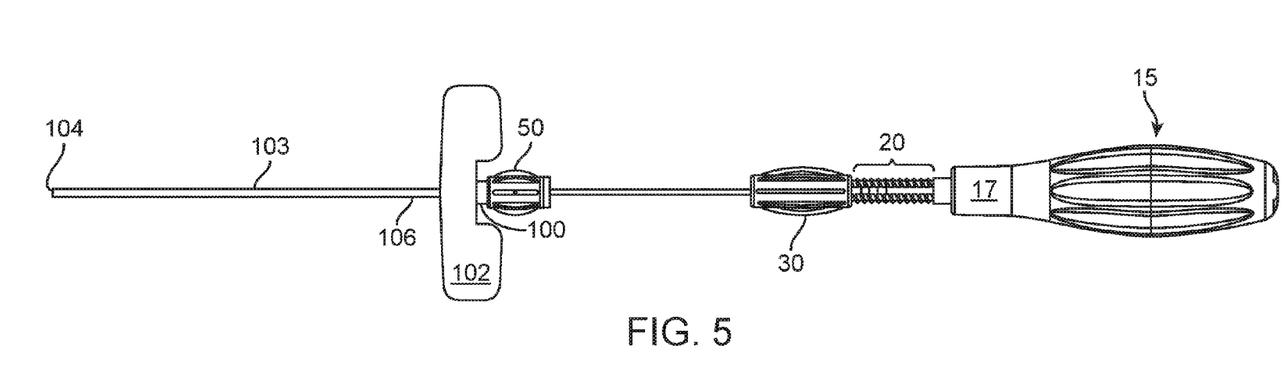
FIG. 5 shows a torque limiting device with extendable memory blade and connector sheath connected to a cannula.

According to some aspects of exemplary implementations, as shown in FIGS. 3 and 4 is a torque limiting device with extendable memory blade 5.

Shaft 10 has a resector blade 11 on a memory arm 12 at its distal end 13 and at its proximal end 14 handle 15 is affixed. Handle 15 may be a fixed mount wherein the affixation of the shaft is such that it moves as the handle is rotated and memory blade resector so rotates. If the memory blade encounters a structure that it is unable to cut and rotational torque is applied past the failure point of memory arm 12 and/or blade 11 the arm and/or blade will break. Alternatively, handle 15 may contain a torque limiting mechanism wherein the affixation of the shaft is such that it moves as the handle is rotated and memory blade resector so rotates. However, if the memory blade encounters a structure that it is unable to cut and rotational torque is applied past the torque limit of the mechanism the torque limiting will disengage the force on the blade and can avoid breakage. Such torque limiting mechanisms are known in the art and applicant hereby incorporates by this reference its issued U.S. Pat. No. 7,938,046 as if fully set forth herein.

Handle 15 at its proximal end has a handle grip 16 and at its distal end 17 a neck 20 is extended. At the remote end of the neck is a shaft mount 22. The neck also may have a threaded nut guide 25 and positional reference marks 27. An adjustable deployment nut 30 with corresponding internal threads 32 may be mounted on said neck. Nut grips 34, shown as ridges, may extend from said nut. Those of ordinary skill in the art will recognize that this disclosure encompasses using a sliding deployment nut which slides along an unthreaded neck and such a design changes is within the scope of this disclosure.

The memory arm 12 is comprised of nitinol or another memory alloy. The natural state of the arm 12 is curved. Accordingly, it is advantageous, in some instances, to preload the blade 11 and memory arm 12 into a hollow sheath 40 whereby the arm 12 is compacted into a substantially elongated position thereby minimizing the cross section of the arm, blade and shaft. The hollow sheath 40 is constructed of a material that is harder than the blade 11 and at its distal end has a tip forming a blade guide 42 of an internal diameter sufficient to house the memory arm 12 in its elongated shape and the blade 11 in a substantially linear position and allow the sheath to slide up and down the shaft 10.

To accomplish a positive mating with a cannula through which the blade 11 is deployed, a sheath sleeve 50 surrounds at least a portion of the hollow sheath 40. The generally hollow sheath sleeve 50 may also be formed as part of the sheath 40. Sleeve gripping elements 52, shown in a non-limiting fashion, may be extended ribs or grips. At the forward end 54 of the sheath sleeve is a mounting guide which mates with a cannula mount and which may be threaded 55. A threaded sheath sleeve opening (TSSO) allows the sheath sleeve and associated sheath to be connected and/or aligned with a cannula (See FIGS. 4 through 7B). In those instances wherein the sheath sleeve and sheath are separate parts, they may be friction fit, glued, sonic welded or otherwise attached to one another. Those of ordinary skill in the art will recognize that this disclosure encompasses using a sliding sheath sleeve whereby the threaded internal section slides on top of a cannula mount.

Additionally, the mounting may be a latch and catch (not shown) to accomplish a positive lock. The threading 55 is one form of a temporary mount. Such a design changes is within the scope of this disclosure.

Prior to attaching a fixed or torque limiting device with shaft having a memory arm and resecting blade to a cannula for use, the threaded forward end 54 of the may be fitted into a cannula mount 100. On the cannula mount is a threaded section (not shown) by which the threaded forward end of the sheath sleeve may be positively attached. As previously noted, a slide on fixation is also within the scope of this disclosure as is latch and catch fitting. In some instances the hollow sheath 40 and the sheath sleeve may be combined into a unitary part which both holds the memory arm and blade in a compressed state and has a mount to connect with the cannula. Such a unitary part is within the scope of this disclosure.

A cannula device 101 which may include a body 102. It has a hollow lumen 103. The lumen may be used to swap out tools used during medical procedures such as trocars, syringes, resectors, irrigation and the like.

FIGS. 5 through 7Bb illustrate a resector being loaded into said lumen 103. The methods and systems disclosed herein in some aspects may be used with very small lumen internal diameters of the order of about 10.2 to 8.3 French. The methods and systems disclosed herein in some aspects may be used with larger lumen internal diameters of the order of about 9.5 gauge and larger or about 9 gauge and larger. The outer diameter o.d. of the shaft 10 for use in an 11 gauge o.d. cannula is smaller than the i.d. of the cannula lumen. The i.d. of the lumen is between about 2.35 mm and 2.37 mm. The outer diameter o.d. of an 11 gauge cannula is about between about 2.7 mm and 3.2 mm and more preferably about 3.05 mm.

The cannula device 101 in addition to a hollow lumen has the disclosed cannula mount 100. The cannula lumen 103 has an unattached distal end 104 and a proximal end 106 attached to said cannula mount 100. The shaft 10, blade 11 and bendable arm in cross section must be small enough to fit through the cannula for deployment through the cannula to a worksite during a procedure. The cannula mount is a temporary or reversible mount which may be a friction fit, a slide fit, a threaded fit or a latch and catch.

Figure 6A:
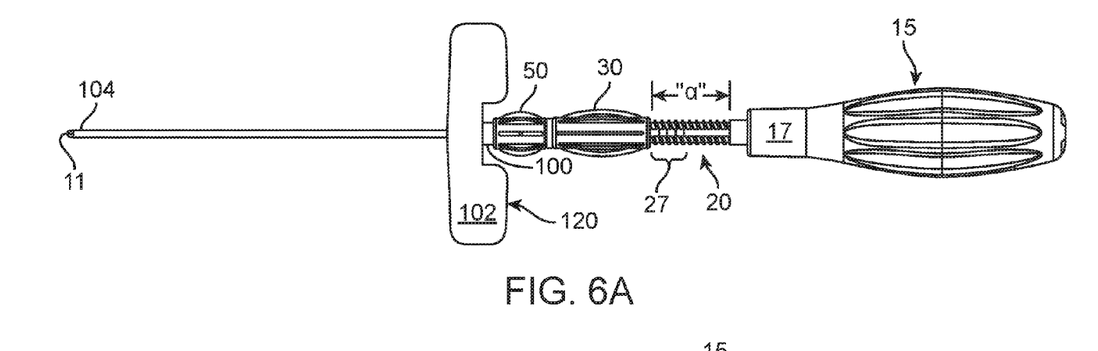
FIGS. 6A and 6B show a side and front perspective views of a torque limiting device with extendable memory blade and connector sheath loaded into a connected to a cannula but not deployed.
Figure 7A:
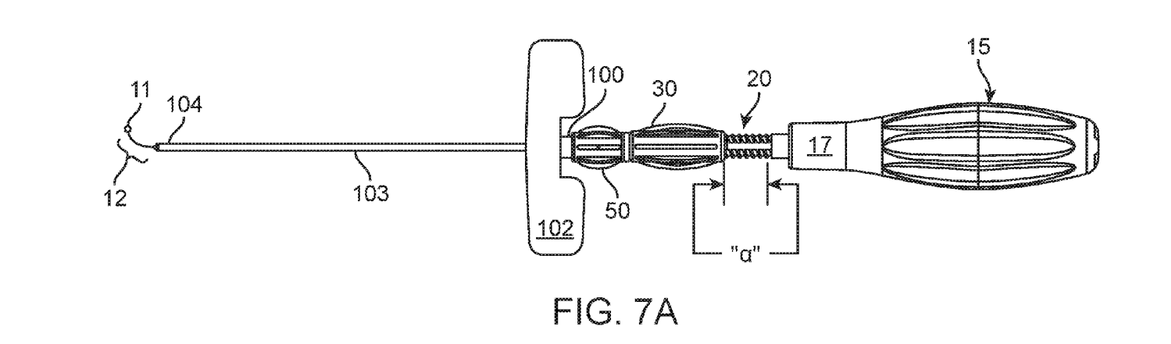
FIGS. 7A and 7B show a side and front perspective views of a torque limiting device with extendable memory blade and connector sheath loaded into a connected to a cannula and deployed.
Figure 7B:
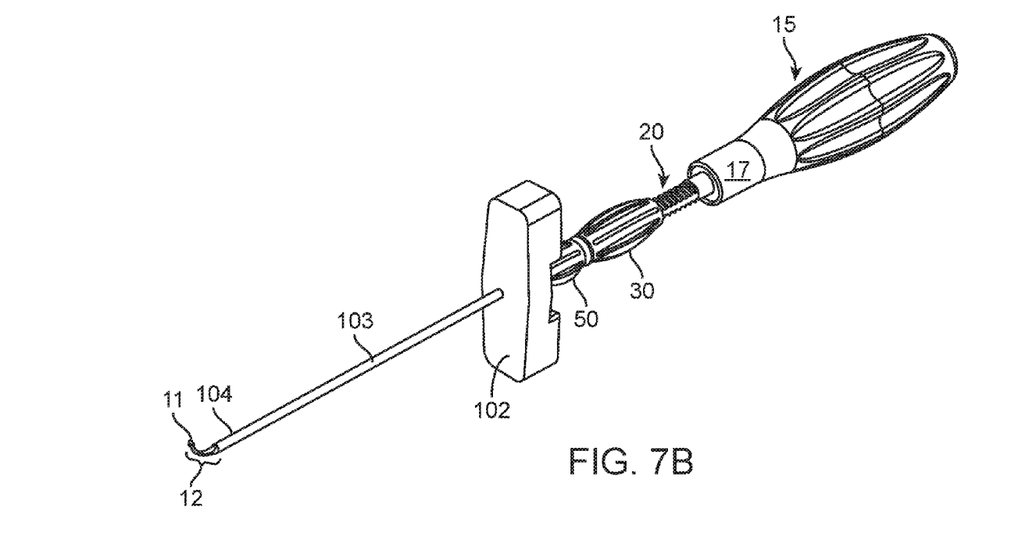
Figure 8:
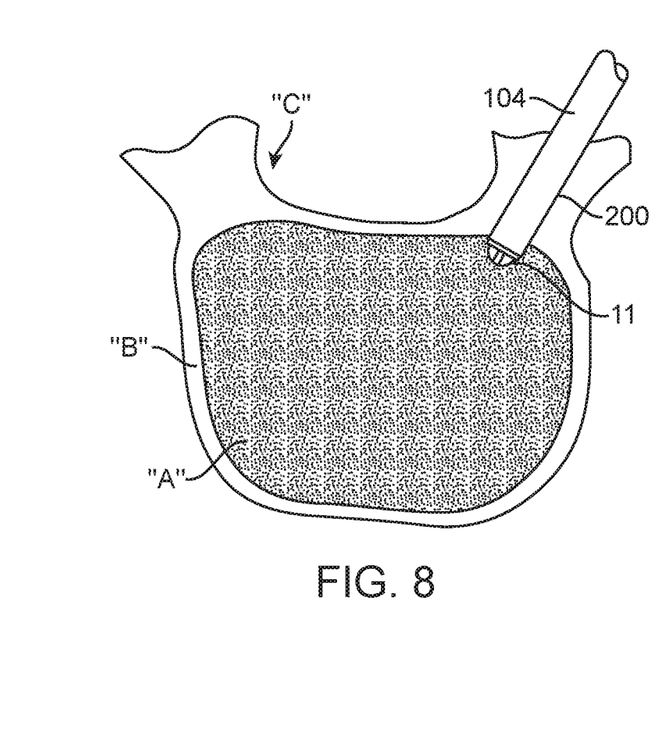
FIGS. 8-11 illustrate the removal of cancelleous bone via a device with a movable extendable memory blade introduced through an 11 gauge cannula and deployed.
Figure 9:
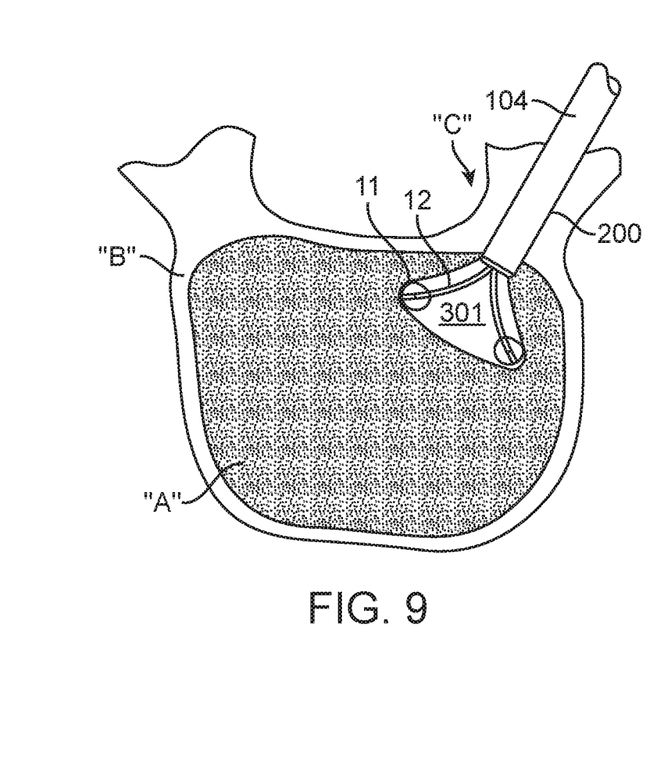
Figure 10:
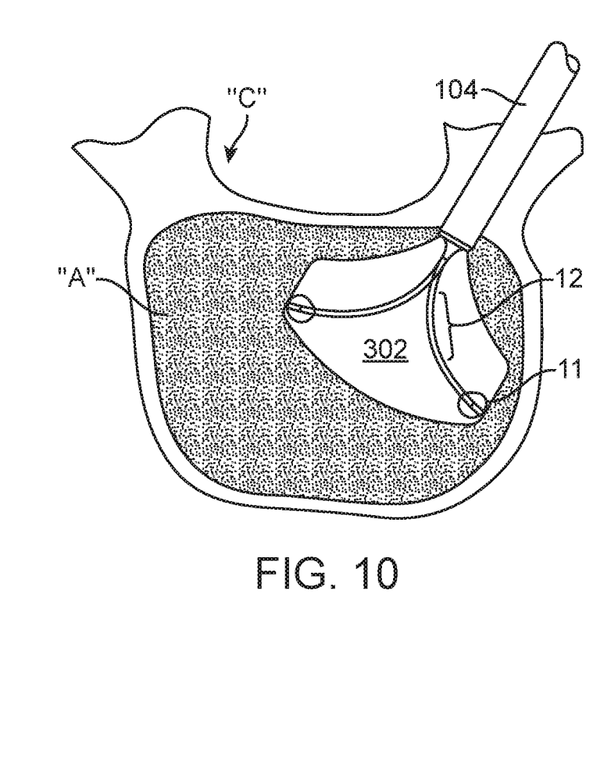
Figure 11:
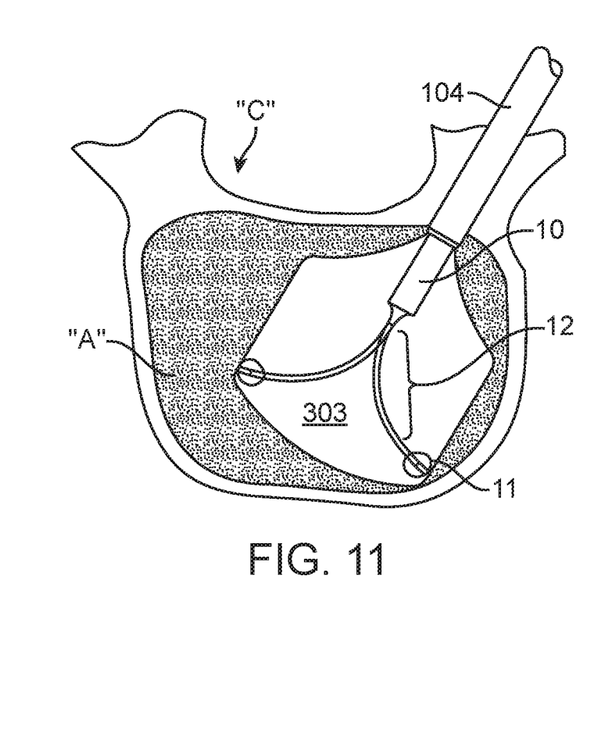

In FIGS. 6A and 7B, the fixed or torque limiting device with shaft having a memory arm and resecting blade is fully inserted into the cannula device. Critical during any medical procedure is the ability to know where a resecting instrument is. In the case of minimally invasive surgery the resecting tool is normally outside the field of unaided viewing.

Disclosed herein is a system to provide unaided visual feedback of blade position during minimally invasive surgery. The method includes fitting the resecting device 5 to a cannula 101 and loading said resecting device into said cannula so that the blade is at the distal end 104 of the cannula but not deployed. Disclosed herein is a system to provide unaided visual feedback of blade position during minimally invasive surgery. The method includes fitting the resecting device 5 to a cannula 101 and loading said resecting device into said cannula so that the blade is at the distal end 104 of the cannula and deployed. One or more positional reference marks 27 such as lines, are placed at intervals on the neck 20. In those implementations wherein the neck 20 is threaded 25 by rotating the deployment nut 30 one direction or the other the visible length of neck changes as represented by measurements "α" and "α'."

Figure 6B:
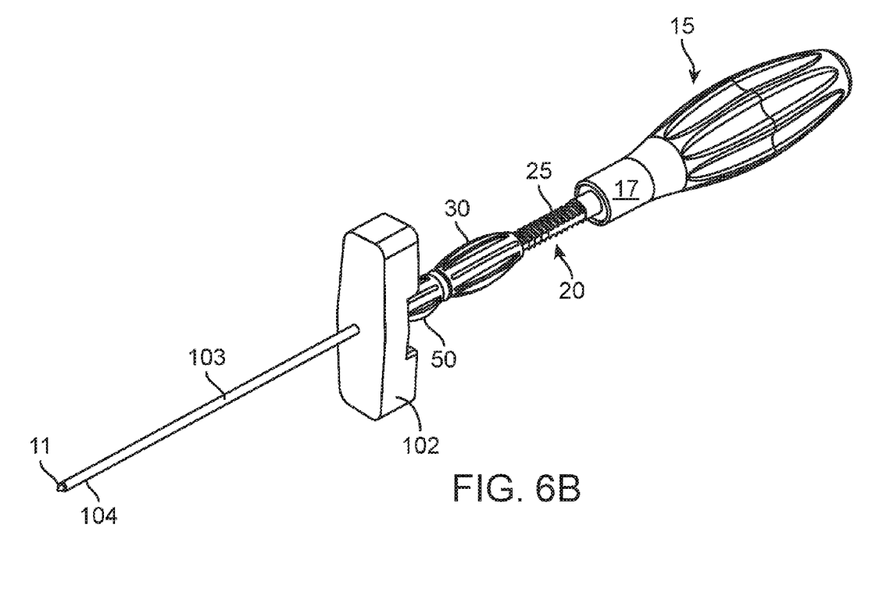

In FIGS. 6A and 6B the resector remains within the cannula and is not deployed—in this instance that position corresponds to a series of visual reference marks 27. Shown in FIGS. 7A and 7B is the deployed Resector, wherein the blade 11 and the memory arm 12 are extended through the distal end 104 of the cannula 101. Because the memory arm has a naturally curved state as the shaft 10 is urged forward by moving the deployment nut 30 the portion of the memory arm 12 extending from the distal end if the cannula returns to its naturally curved state.

FIGS. 8 through 11 are illustrations of the use and method of a fixed or torque limiting device with shaft having a memory arm and resecting blade to a cannula for use in vertebral surgery. Those of ordinary skill in the art will recognize that the indication of use of this disclosure in a particular surgery wherein an about 11 gauge cannula is used is not a limitation. The method and system herein could be used with larger cannulas and/or on other surgical sites and such is within the scope of this disclosure.

The distal end 104 of the cannula is shown inserted through cortical rim bone "B" of a vertebral body and into the cancelleous bone "A." Prior to insertion a passageway 200 is cut. Cutting may be via drill, burr, trocar or the like. The cannula provides a hot swappable entry port via the lumen 103 to swap out, for example, a trocar and replace it with a resector device 5. The disclosed connection method and system provides a positive lock to easily insert a compacted blade 11 and arm 12 assembly into the cannula 103 in a compacted state. If the arm 12 and blade 11 where in a bent state it is more likely the cannula will be dislocated and/or jostled when trying to insert and compact a memory arm and blade into the lumen 103. Unintended movement and jostling of the cannula in a body is undesirable.

In its undeployed state, the blade 11 remains substantially in the lumen 103 co-axial and at the distal end 104. The blade 11 may be in contact with the cancelleous bone "A". As the deployment nut is rotated or slid closer to the handle 15 the shaft 10 is moved forward in the lumen 103 and the blade 11 and memory arm 12 extend. During extension a first region of resected material 301 may be created by rotating the curved memory arm 12 and attached blade. As the deployment nut is rotated or slid yet closer to the handle 15 the shaft 10 is moved forward in the lumen 103 and the blade 11 and memory arm 12 further extend. During further extension a second region of resected material 302 may be created by rotating the curved memory arm 12 and attached blade. As the deployment nut is rotated or slid yet closer to the handle 15 the shaft 10 is moved forward in the lumen 103 and the blade 11 and memory arm 12 further extend and the shaft 10 may also enter the vertebral body "C." During further extension a third region of resected material 303 may be created by rotating the curved memory arm 12 and attached blade.

The resector device may be removed at any time via the co-axial hot swappable method and resected material may be aspirated out. Additionally, the area may be irrigated, and adhesive or cement or antibiotic or a plethora of material may be added. After aspiration or irrigation, the resector device may be reattached and the resecting process may continue.

Figure 12:
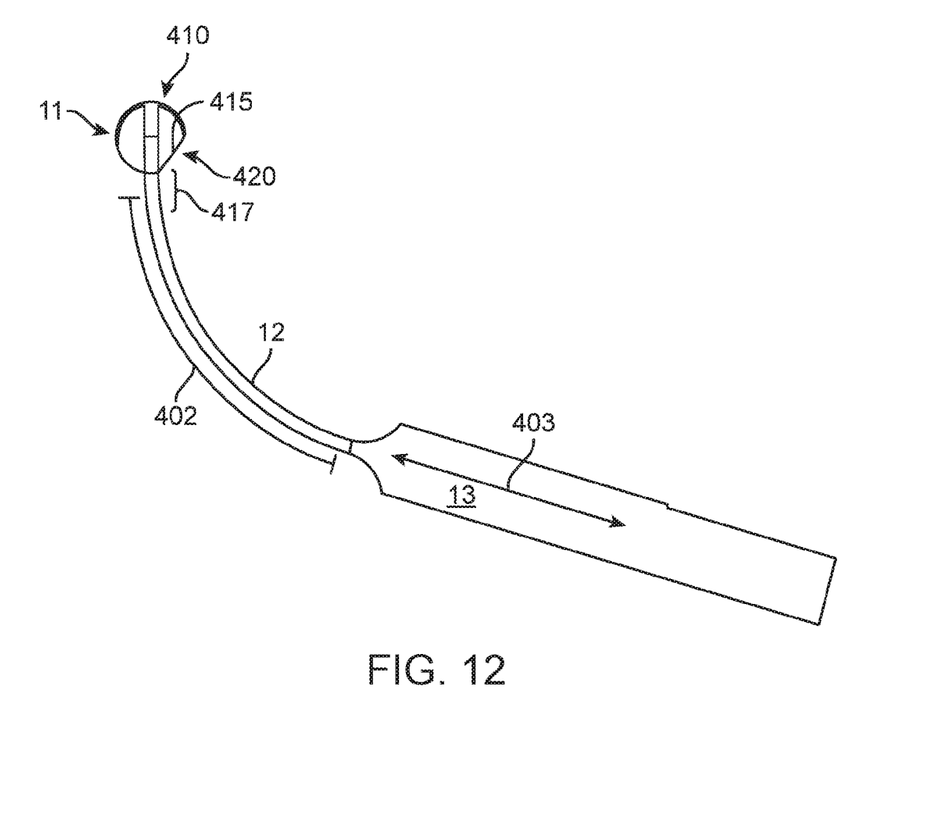
FIG. 12 shows dimensions of one variation of an extendable memory blade for use in an 11 gauge cannula.

FIG. 12 illustrates a side view of a memory arm in a relaxed, non-compacted state. The memory arm 12 is formed between the distal end of the shaft 13 and the blade end 11. The radius 402 represents how far off axis 403 the memory arm is in its relaxed state. The thickness of the memory arm is preferably in the range of about 0.012 to about 0.092 inches and more preferable in the range of about 0.017 inches to about 0.023 inches. The radius 402 is preferable in the range of about 10 degrees to 70 degree and more preferable between about 30 degrees and 50 degrees. There is always a trade off on thickness which provides greater strength and flexibility because the memory arm must compact back into the cannula to remove the device from the vertebral body. To facilitate that removal of the device the blade 11 may have a trailing edge 415 that is angles no more than about 70 degrees from the neck portion 416 adjacent to it. That trailing edge helps to urge the blade into the cannula lumen 103

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure, both independently and as an overall system, and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising," are intended to imply the inclusion of a stated element or step or group of elements or steps, but not the exclusion of any other element or step or group of elements or steps.

Such terms should be interpreted in their most expansive forms so as to afford the applicant the broadest coverage legally permissible.

The invention claimed is:

1. A device to perform minimally invasive surgery on a vertebral body using an 11 gauge cannula, the system comprising:
    a handle (15) with a shaft (10) less than the internal diameter (i.d.) of an 11 gauge cannula having a memory arm (12) with a blade (11) attached thereto;
    said memory arm compactable to a substantially co-axial position within a cannula;
    a hollow sheath (40) with a forward tip (42) having an i.d. substantially the same as the diameter of an 11 gauge cannula;
    said memory arm compacted into said hollow sheath (40);
    an 11 gauge cannula (103) having a distal (104) and a proximal end (106);
    the cannula having an interior diameter substantially the same as the i.d. of said hollow sheath; and,
    whereby aligning the tip and the proximal end of the cannula provides a pathway for the compacted memory arm and blade to be passed in a compacted state from the hollow sheath into the cannula, wherein the hollow cannula further comprises a mounting (100) corresponding to the forward tip; and,
    a sheath sleeve (50) with a forward end (54) that fits over at least a portion of the hollow sheath and the mounting of the hollow cannula.

2. The device of claim 1 wherein the sheath sleeve and hollow sheath are a unitary piece having the i.d. of the hollow sheath and the corresponding threading of the sheath sleeve.

3. The device of claim 2 further comprising sleeve gripping elements (52) extended radially around the sheath sleeve.

4. The device of claim 3 further comprising sleeve gripping elements extended radially around the unitary hollow sheath and sheath sleeve.

\* \* \* \* \*

UNITED STATES PATENT AND TRADEMARK OFFICE
CERTIFICATE OF CORRECTION

PATENT NO.        : 9,603,673 B2
APPLICATION NO.   : 15/298812
DATED             : March 28, 2017
INVENTOR(S)       : John Nino and David Ivinson It is certified that error appears in the above-identified patent and that said Letters Patent is hereby corrected as shown below:

Please correct the title to read as follows:
CO-AXIAL HOT SWAPPABLE SYSTEM FOR MINIMALLY INVASIVE MEDICAL PROCEDURES Signed and Sealed this
Tenth Day of July, 2018

Andrei Iancu
*Director of the United States Patent and Trademark Office*